United States Patent [19]
Asher

[11] Patent Number: 5,573,400
[45] Date of Patent: Nov. 12, 1996

[54] EXPANDING DENTAL WEDGE

[76] Inventor: Randall S. Asher, 8756 S. Aberdeen Cir., Highlands Ranch, Colo. 80126

[21] Appl. No.: 350,430

[22] Filed: Dec. 6, 1994

[51] Int. Cl.⁶ ..................................... A61C 5/14
[52] U.S. Cl. .............. 433/136; 433/149; 433/80
[58] Field of Search .................... 433/149, 136, 433/80

[56] References Cited

U.S. PATENT DOCUMENTS

| | | | |
|---|---|---|---|
| 2,867,905 | 1/1959 | Meacham | 433/149 |
| 3,510,948 | 5/1970 | Walthall | 433/149 |
| 3,815,243 | 6/1974 | Eames | 433/149 |
| 3,890,714 | 6/1975 | Gores | 433/149 |
| 4,198,977 | 4/1980 | Aoki | 433/136 |
| 4,259,070 | 3/1981 | Soelberg | 433/149 |
| 4,337,041 | 6/1982 | Harnseny | 433/149 |
| 4,468,199 | 8/1984 | Wikel | 433/149 |
| 4,469,199 | 8/1984 | Weikel | 433/149 |
| 4,565,722 | 1/1986 | Highgate et al. | 433/226 |

*Primary Examiner*—Cary E. O'Connor

[57] ABSTRACT

An expanding dental wedge structure to be used in association with dental matrix bands as used for placing dental restorative materials. The pre-expansion shape in cross section is roughly triangular with the dimensions of the triangle decreasing along the length ending in a pointed manner (FIG. 1). The wedge (FIG. 1) is to be inserted into the area between teeth, one of which is carrying a matrix band. After insertion, the wedge is exposed to moisture causing pronounced expansion (FIG. 2), which through equal pressure on the tooth surfaces and gingival tissues involved does: (a) press the matrix tightly against the tooth sealing out moisture contamination, (b) absorb moisture, drying the surgical field, and (c) decreases blood flow and subsequent bacterial and vital transmission.

1 Claim, 1 Drawing Sheet

EXPANDING DENTAL WEDGE

BACKGROUND-FIELD OF INVENTION

This invention relates the dental wedge, specifically those used to secure matrix retainers during placement of dental materials for restoration of proximal dental decay.

BACKGROUND-DESCRIPTION OF PRIOR ART

Restoration of proximal dental decay (cavities between teeth) is a very common practice in dentistry. After removal of the carious lesion, a matrix band is inserted between the teeth to hold the restorative materials in place and to act as mold for proper tooth shape.

For some time, the matrix band has been secured in position by the insertion of an elongated wood wedge. The wedge was held in place by pressure from the adjacent teeth and interdental gingival tissues. Unfortunately, these wedges are most often flat on the sides of the elongation. Since tooth contours are highly variable, there is significant pressure in only one area of the matrix band where the convexity of the tooth is the most pronounced. Other areas of the matrix band are held in place with only mild pressure or no pressure. The result is a loose fit in which saliva, blood, and other contaminants are allowed to flow into the cavity preparation. Since dental restorative materials only function optimally when dry, the service and longevity of the restoration are compromised. Also, the insertion of the ridged wedge is detrimental to interdental gingival tissues.

Although multiple patent applications have been filed, inventors have not adequately solved the problem of uneven pressure or no pressure on the matrix band.

U.S. Pat. No. 3,510,948 to Walthall (1970) discloses only an improvement in how to remove the wood wedge, not how to provide a better seal.

U.S. Pat. No. 3,815,243 to Eames (1974) attempted to solve the problem by the addition of small raised areas of the sides of the wedge to more evenly distribute the pressure. However, the wedge is expensive to produce and does not provide any improvement over conventional wedges since the raised portions crush upon insertion, rendering the device not superior to conventional wedges.

U.S. Pat. No. 3,890,714 to Gores (1975) attempted to solve the problem by using a folded plastic wedge. The device has never gained acceptance since the thin walls were destructive to gingival tissues. This product does not provide any improvement to conventional wedges and may be more destructive to gingival tissues, since conventional wedges crush the interdental tissues and the device lacerates gingival tissues.

U.S. Pat. No. 4,259,070 to Soelberg (1981) uses a duel wedge system where a part of the wedge is inserted from both sides of the arch and joined midway of the preparation. The item is exceptionally expensive to produce, difficult to use, and provides little or no benefit over conventional wedge systems.

U.S. Pat. No. 4,337,041 to Harnseny (1982) attempts to solve the problem of loose band fit by creating a wedge to the shape of the interproximal tooth surfaces. This wedge, although unique, fails to account for the multitude of different interproximal tooth shapes. Also, the depressions to approximate the interproximal surfaces are generally too fine in nature and will not provide adequate pressure against the band to withstand the pressure of the insertion of restorative materials.

U.S. Pat. No. 4,468,199 to Wikel (1984) attempts to solve the problem of gingival bleeding by impregnating the wedge with a hemostatic solution. Unfortunately, this still did not solve the basic problems of a loose band fit and damage to gingival tissues.

A clear plastic wedge has been marketed, with the idea of being used with light-cured restorative materials. Although light does travel through the wedge, the same limitations are present as with all other wedges produced to date.

OBJECTS AND ADVANTAGES

Accordingly, besides the objects and advantages of the expanding dental wedge listed in my above patent, several objects and advantages of the present invention are:

(a) to provide a wedge that can absorb moisture and therefore prevent it from contaminating dental restorations;

(b) to provide a dental wedge which when used provides a seal between the matrix band and the tooth being restored;

(c) to aid in the elimination of bacterial and viral transmission by decreasing the amount of blood produced from dental procedures through gentle pressure on gingival tissues, thus displacing gingival tissues; and (d) to provide a dental wedge whose production allows for the efficient and rapid restoration of interproximal dental caries.

Still further objects and advantages will become apparent from a consideration of the ensuing description and drawings.

DRAWING FIGURES

Figure 1:
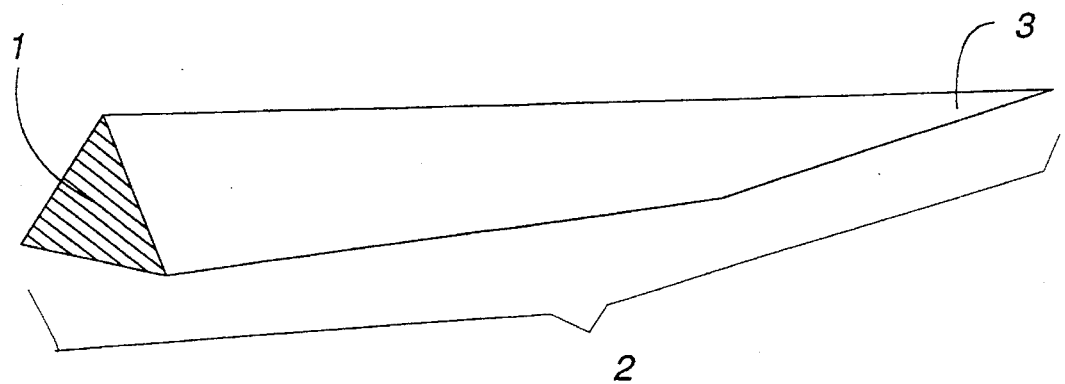
FIG. 1 shows the pre-expansion wedge shape which is roughly triangular with the dimensions of the triangle decreasing along the length ending in a pointed manner.

REFERENCE NUMERALS IN DRAWINGS 1 base of wedge 2 elongated shape wedge with decreasing triangular size 3 point of wedge 4 flat sides of wedge 5 wedge inserted and expanded between teeth 6 matrix band 7 teeth to be restored

DESCRIPTION-FIGS. 1 AND 2

A typical embodiment of the expanding dental wedge, before expansion, of the present invention is illustrated in FIG. 1. The pre-expansion wedge consists of an elongated body with three longitudinally extending sides and a taper from the thick end to a point (FIG. 1). The expanding dental wedge is composed of compressed dried absorbent material, such as cellulose, with a non-toxic water soluble binder, such as vegetable products or another water soluble binder. The wedge may consist of any other suitable material that expands in contact with moisture. Any of a number of antibacterial, hemostatic or other substances as desired can be incorporated into the wedge due to the porous nature of the material used in the manufacture of the wedge.

The pre-expansion shape in cross section is roughly triangular with the dimensions of the triangle decreasing along the length ending in a pointed manner. The width of the sides on the larger end can be approximately 0.5 mm to 2 mm depending on the distance between the proximal surfaces of the teeth necessitating a change in initial wedge dimension to obtain reciprocal pressure on the proximal tooth surfaces.

Figure 2:
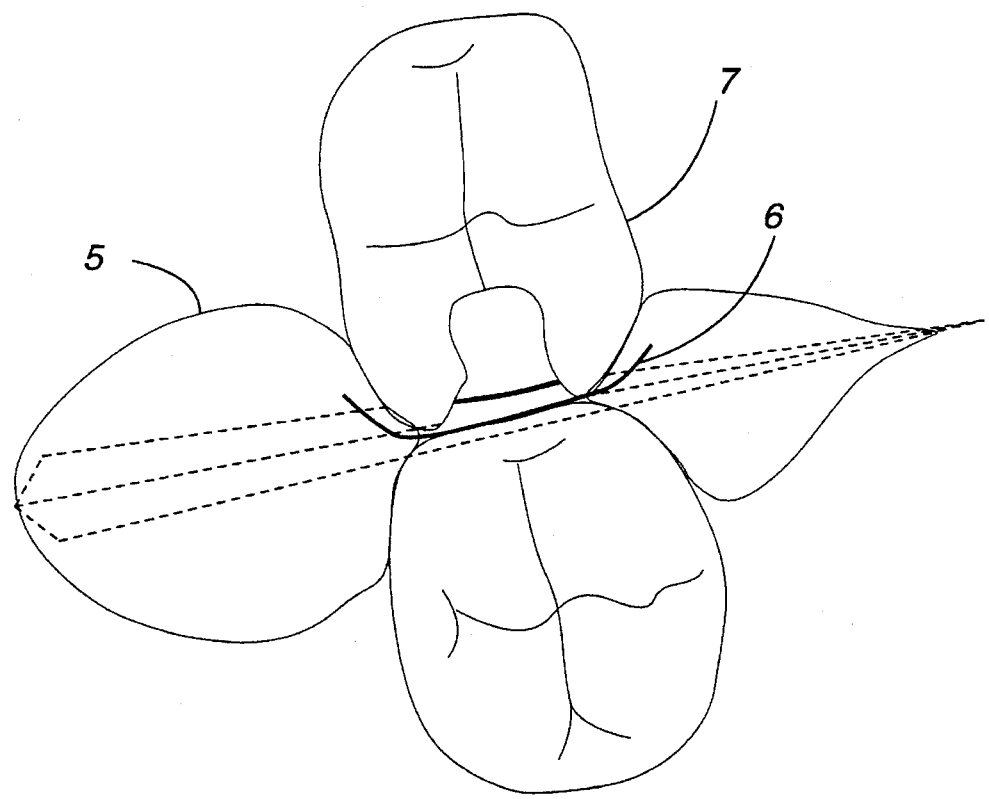
FIG. 2 shows the post-expansion wedge inserted in the interproximal of the teeth to be restored.

Post-expansion dimensions are variable depending on the width and anatomy of the proximal surfaces involved (FIG. 2). From the description above, a number of advantages of my expanding dental wedge become evident:

(a) This wedge is much more gentle to interdental gingival tissues due to its pliable nature when in contact with moisture;

(b) The wedge is economical to produce since standard milling techniques can be used to produce the shape desired; and (c) The wedge can be used as a delivery system for drugs or other substances which might be needed to aid in dental restorative techniques.

OPERATION-FIGS. 1 AND 2

The manner of using the expanding dental wedge (FIG. 1) is identical to that for most other dental wedges in use. During the process of filling interproximal cavity preparations and after the placement of the matrix band, the wedge is inserted in the interproximal area between the teeth. Using gentle pressure from a finger or a dental instrument until resistance is felt.

With the expanding dental wedge, a second step is required— the addition of small amounts of moisture to begin the expansion process. This moisture may be applied by the dentist in the form of water or moisture from the interproximal gingival tissues may prove sufficient for expansion. Said moisture causes a pronounced expansion of the compressed material, providing reciprocal pressure to all points of the matrix band along the proximal surface, thus providing a matrix band seal (FIG. 2). Moisture contamination is prevented by absorbing potential moisture before it can contaminate the cavity preparation. Also, the expanding dental wedge provides reciprocal pressure to compress the gingival tissues, restricting blood flow and fluid volume, further reducing the amount of moisture available for contamination of the cavity preparation.

SUMMARY, RAMIFICATIONS, AND SCOPE

Accordingly, the reader will see that the expanding dental wedge of this invention can be used to quickly and efficiently prevent moisture during the placement of dental restorative materials and hold the matrix band in place and sealed against the tooth surface. In addition, the expanding dental wedge can decrease the transmission of bacterial and viral agents due to a restriction in blood flow to the operative field during dental restorative procedures.

Although the description above contains many specificities, these should not be construed as limiting the scope of the invention but as merely providing illustrations of some of the presently preferred embodiments of the invention. For example the expanding dental wedge may have other shapes: oblong, square, round, trapezoidal etc. The shapes can be sculpted to the anatomy of teeth or gingiva. The expanding material may be composed of synthetic foams, cellulose, or any other compressible material which expands if given the right stimulus.

Thus, the scope of the invention should be determined by the appended claims and their legal equivalents, rather than the examples given.

I claim:

1. A method for preventing moisture contamination of dental cavity preparations comprising the steps of:

a. securing a matrix band against the tooth by inserting a device composed of compressed hydrophilic material into proximal tooth areas, securing the matrix band against the tooth by reciprocal pressure against each tooth, and b. decreasing moisture contamination by absorbing potential moisture with said device before said moisture can contaminate the cavity preparation, and c. wherein pronounced expansion of the compressed material provides reciprocal pressure to all points of the matrix band along the proximal surface resulting in a close adaption of the matrix band to the tooth surface.

* * * * *